United States Patent [19]

Heemels et al.

[11] Patent Number: 5,603,331
[45] Date of Patent: Feb. 18, 1997

[54] DATA LOGGING SYSTEM FOR IMPLANTABLE CARDIAC DEVICE

[75] Inventors: Jan P. Heemels, Minneapolis; Gerrard M. Carlson, Champlin; Julio C. Spinelli, Shoreview, all of Minn.

[73] Assignee: Cardiac Pacemakers, Inc., St. Paul, Minn.

[21] Appl. No.: 600,133

[22] Filed: Feb. 12, 1996

[51] Int. Cl.$^6$ .................................................. A61B 5/0452
[52] U.S. Cl. .................................................. 128/696; 607/25
[58] Field of Search .................................. 128/696, 703, 128/706, 708; 364/413.06

[56] References Cited

U.S. PATENT DOCUMENTS

| | | | |
|---|---|---|---|
| 4,974,598 | 12/1990 | John ........................................ | 128/696 |
| 5,088,488 | 2/1992 | Markowitz et al. ...................... | 128/706 |
| 5,277,189 | 1/1994 | Jacobs ..................................... | 128/696 |
| 5,291,400 | 3/1994 | Gilham ................................... | 364/413.06 |
| 5,299,119 | 3/1994 | Kraf et al. ............................... | 128/696 |
| 5,411,031 | 5/1995 | Yomtov ................................... | 128/706 |

OTHER PUBLICATIONS

Coumel et al., "Heart Rate and Heart Rate Variability in Normal Young Adults", J. Cardiovascular Electrophysiology, vol. 5, No. 11, Nov. 1994, pp. 899-911.

Ori, et al., "Heart Rate Variability", Clinics, vol. 10, No. 3, Aug. 1992, pp. 499–537.

Moser, et al., "Heart Rate Variability as a Prognostic Tool in Cardiology", Circulation, vol. 90, No. 2, Aug. 1994, pp. 1078–1082.

Primary Examiner—William E. Kamm
Assistant Examiner—George R. Evanisko
Attorney, Agent, or Firm—Haugen and Nikolai, P.A.

[57] ABSTRACT

An implantable cardiac rhythm management device (pacemaker or defibrillator) having circuitry for determining the interval between two successive natural ventricular depolarization signals, includes the capability of computing and storing histogram arrays of heart rate variability data over a prolonged period, such as 24 hours. By utilizing an algorithm for generating a histographic log and a time domain log wherein a logarithmic data compression technique is implemented, the volume of HRV data collected for later telemetered readout to an external device does not exceed the memory and power capabilities of the implanted device.

23 Claims, 6 Drawing Sheets

NORMAL HEART

DISEASED HEART

DATA LOGGING SYSTEM FOR IMPLANTABLE CARDIAC DEVICE

BACKGROUND OF THE INVENTION

I. Field of the Invention

This invention relates generally to medical electronic diagnostic and/or treatment apparatus and more particularly to an implantable device having means for logging heart rate variability data over extended time periods for subsequent read-out and analysis.

II. Discussion of the Prior Art

Currently available implantable cardiac pacemakers and defibrillators are capable of collecting and storing a variety of information relating to the instantaneous electrical response of the heart and providing this information in real time, via telemetry link, to an external programmer which may readily be equipped with substantial data processing, storage and display resources. Certain other implantable devices are capable of logging a limited amount of parametric data, typically in the form of various event counters, which is retained in the device for future telemetry and analysis. These arrangements provide useful, but limited, information regarding the status of the heart or progression of the disease.

Accurate diagnosis requires evaluation of extensive data over an extended period of time. Long-term telemetry of raw data from an implanted device is undesirable because the low energy available to the implanted transmitter requires that the external receiver be worn by the patient in close proximity to the implanted device. Even then, the transmission of voluminous raw data may prematurely deplete the implanted battery. The preferred device currently used for logging diagnostically useful cardiac data is known as a Holter monitor. It is an external data recorder which monitors and stores cardiac electrical data sensed via surface EKG electrodes. It is desirable to incorporate the data logging function exemplified by the Holter monitor into the implantable pacemaker. However, generally speaking, prior art implantable cardiac devices, such as pacemakers, lack the memory capacity to store the voluminous raw data and/or the power to telemeter it. Well known signal compression techniques offer insufficient compression.

Lossless signal compression techniques, such as run length encoding, are well known. Since only redundant elements of the signal are eliminated all of the raw data is recoverable from the compressed signal with exactly the same resolution that it was quantized. However, all lossless compression techniques suffer from an insufficient compression ratio and an intolerable processing load. The highest compression ratios are achieved by first extracting a feature, or set of features, from the raw data, which is well correlated to the cardiac diagnostic process, and then employing lossy compression on the extracted features. Ideally, lossy data compression allows most of the data to be discarded, preserving only the minimum set of data required to adequately characterize the extracted features.

Heart Rate Variability (HRV) has been identified as a feature of cardiac activity which is particularly useful for both diagnosis and prognosis. HRV is defined as a measure of the beat-to-beat variance in sinus cycle length over a period of time. It is used as a measure of parasympathetic tone. It has been determined that individuals with diminished HRV have reduced vagal tone and probably are at increased risk of death following myocardial infarction. Various researchers have employed spectral analysis to characterize HRV. (See Coumel et al., "Heart Rate and Heart Rate Variability in Normal Young Adults", *J. Cardiovascular Electrophysiology*, Vol. 5, No. 11, November 1994.) Others have elected to characterize Heart Rate Variability by considering the beat-to-beat variability in heart rate. (See Ori, et al., "Heart Rate Variability", *Clinics*, Vol. 10, No. 3, August 1992.) This beat-to-beat characterization has been expanded to a two-dimensional histogram which displays the probability density function of the absolute beat-to-beat interval difference as a function of interval. The process of forming such a two-dimensional histogram is defined as "binning". This process will be subsequently described in detail. In summary, although the prior art shows several ways that heart rate variability data, accumulated over an extended period of time, may be processed to make the data more understandable to a clinician, we are not aware of any teaching of how logging of HRV data might be accomplished within an implantable pacemaker.

OBJECTS OF THE INVENTION

It is an object of this invention to provide a method and apparatus for very efficiently processing, logging and disseminating the essential features relating to HRV accumulated from a continuous long term monitoring of cardiac activity. The method is sufficiently conservative of data memory, program memory and power consumption that it may be incorporated within an implantable pacemaker to log a 24 hour period of cardiac activity accumulated for subsequent telemetry. The 24 hour data can be converted to a single index through calculation of a standard deviation. These standard deviations can be stored for long-term trend analysis.

It is a further object of this invention to provide a method of processing and displaying HRV data received via telemetry from the microprocessor in a manner most easily understood by a clinician and which will provide the greatest graphical contrast between a normal and an abnormal HRV pattern, for example, in a sick heart.

SUMMARY OF THE INVENTION

Referring to FIG. 1(a), a two-dimensional histogram indicative of the rate variability of a normal heart over a 24 hour interval is illustrated. The X axis corresponds to the interval between an instant pair of consecutive heartbeats with the interval increasing from left to right. The Y axis corresponds to the absolute difference between the instant interval and the immediately preceding interval with the difference increasing from the background to the foreground. The X axis and the Y axis are quantized into bins to form the two-dimensional histogram. The Z axis corresponds to the base 2 logarithm of the frequency of occurrence for each bin. The resulting histogram has the appearance of a mountain with foothills projecting to the right and front. The mountain corresponds to the more typical cardiac interval variations while the foothills correspond to the more atypical and varied activity. It is believed that the entire texture of this histogram is diagnostically useful. The spatial and quantitative relationship of the foothills to the mountain is of particular interest. FIG. 1(b), showing a corresponding presentation for a diseased heart, provides support for this belief. Note that the diseased heart exhibits much less variability. Even without considering the beat-to-beat interval variations, there is less variability of the intervals themselves as shown by the higher and narrower peak for the diseased heart. Further, the foothills indicative of beat-tobeat variability are absent. Logarithmic compression of the Z axis greatly enhances the contrast between FIGS. 1(a) and 1(b) in that the foothills are effectively magnified while the essential information regarding the shape of the mountain is preserved. Fortuitously, the logarithmically compressed binning also yields a very high degree of data compression which can be accomplished with a computationally simple process.

In a preferred embodiment of the invention, an implantable stimulator, such as a pacemaker or defibrillator or monitoring device, processes and logs multiple sets of two-dimensional histogram data similar to what is plotted in FIG. 1. Data is accumulated only for sensed beat intervals and not any intervals associated with paced events. Each set corresponds to a fraction of a day and there are a sufficient number of sets to continuously span a 24-hour interval. One possibility may comprise 24 one-hour sets. Hereafter, the data accumulated in this manner over a 24-hour interval will be referred to as the histographic log. Data accumulation is preferably initiated by a telemetry command and proceed automatically to completion. Alternatively, an ongoing mode of logging could be initiated which terminates in response to a particular cardiac condition sensed by the pacemaker. This would provide HRV data coincident with a significant cardiac episode. For either mode, the data is retained for subsequent retrieval via telemetry. The external pacemaker programmer may then develop a display or hard copy presentation of the data. Presentations contemplated include individual histograms for each data set or composite histograms of a plurality of data sets. One particularly useful mode of display, particularly for a video terminal device, is to display the bins of FIG. 1 as a uniform array of squares where the X and Y axes of the display correspond to the X and Y axes of FIG. 1, respectively. The value for each bin, i.e., the Z axis of FIG. 1 is represented as varying colors or shades of grey to thus produce a contour map form of presentation. Alternatively, the data may be displayed as a time lapse graphical display showing motion over, say 24 hours.

A single pair of indices, i.e., the mean value and standard deviation of the absolute value of the beat-to-beat difference provides the best summary characterization of the more detailed information provided by the two-dimensional histogram. These indices may be computed for a substantially shorter period than provided by the histographic log to more thoroughly characterize the short and long term trends of heart rate variability. For example, a 24-hour period may be characterized with 288 pairs of data, each pair computed for a five-minute interval. The data can be accumulated in a one-dimensional, 1152 byte Trend array contained in the RAM memory of the pacemaker. The pacemaker logs the square of the variance to thereby move the computationally intensive burden of performing the square root operation required to compute the standard deviation from the pacemaker to the external pacemaker programmer. Hereafter, the set of indices accumulated in this manner will be referred to as the "time domain log". Although the histographic log and the time domain log each have independent diagnostic value, in a preferred embodiment, a single implantable pacemaker can, alternatively, as commanded via telemetry, generate either log, storing the accumulated data in a common region of memory.

DETAILED DESCRIPTION OF THE INVENTION

Figure 1A:
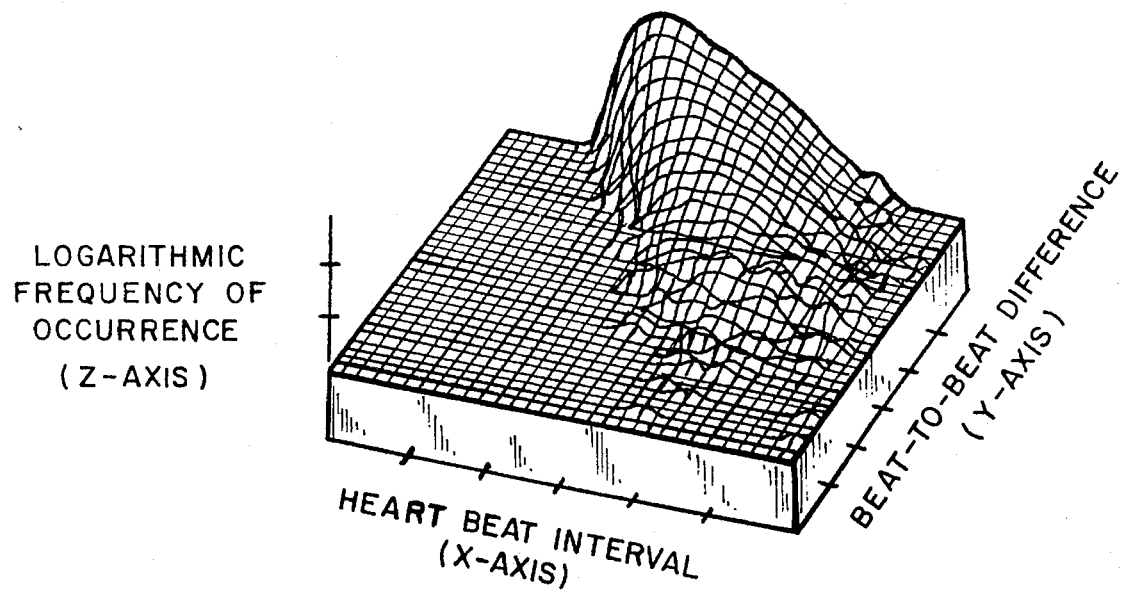
FIG. 1(a) is a two-dimensional histogram of HRV for a normal healthy heart.
Figure 1B:
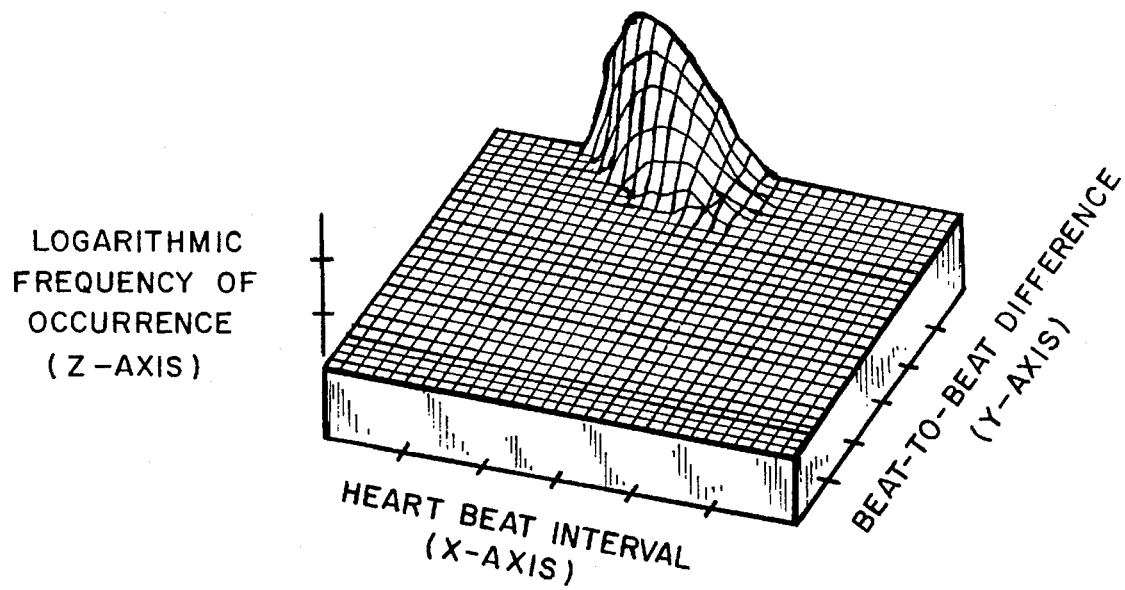
FIG. 1(b) is a two-dimensional histogram of HRV for a sick heart.
Figure 2:
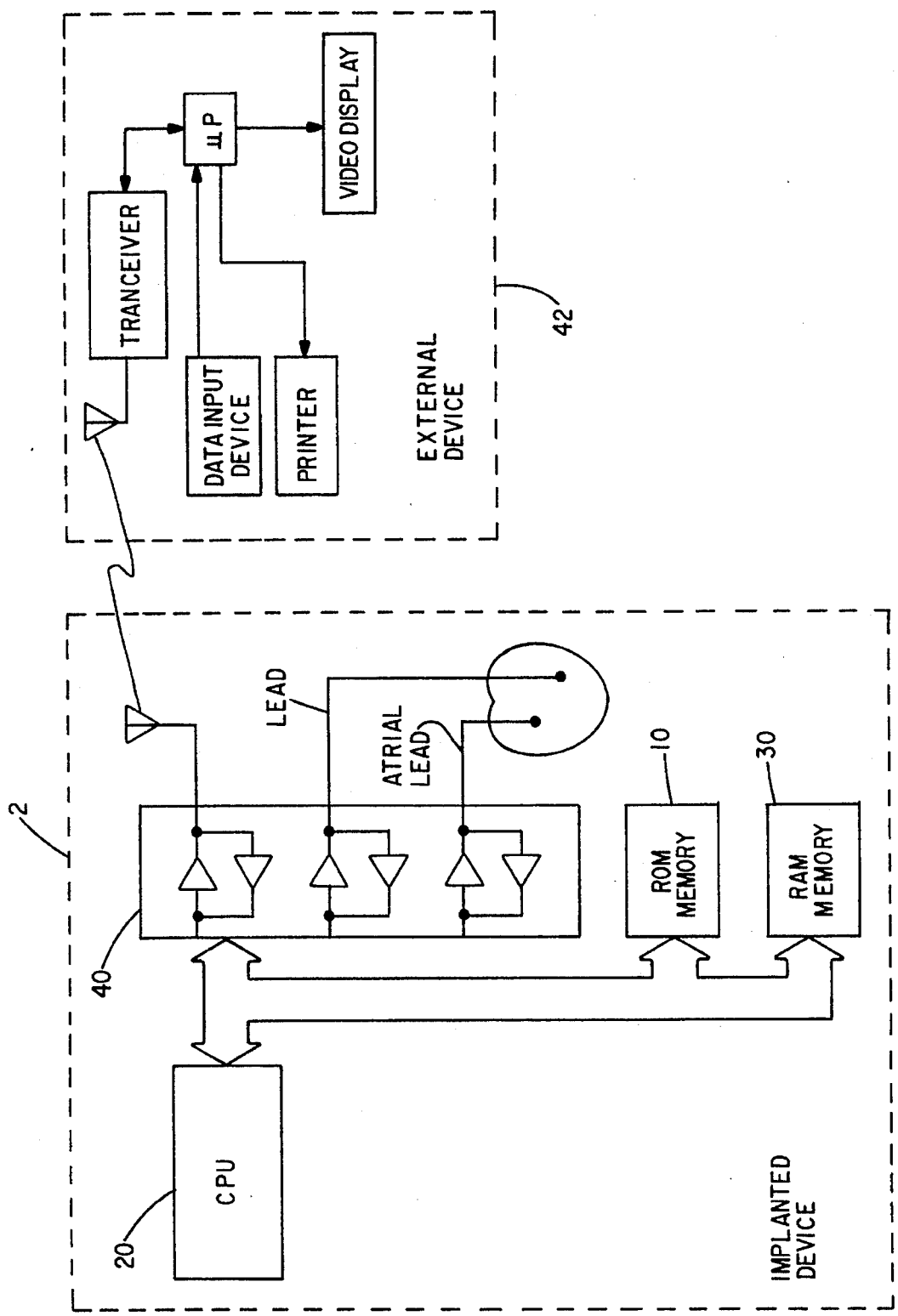
FIG. 2 is a block diagram representation of a DDD pacemaker incorporating the present invention.

FIG. 2 shows a system block diagram of the instant invention. It is representative of a prior art, implantable microprocessor-controlled, dual-chamber demand pacemaker modified to incorporate the invention, but the invention is not limited to this embodiment. implantable pacemaker is shown enclosed by dashed line box 2 Either Read Only Memory 10 or RAM memory 30 contains a program which is executable by Central Processing Unit 20 to perform the well-known functions of DDD pacing and telemetry of data stored in memory 30 to an external programmer device enclosed by dashed line box 42. The programmer 42 is entire conventional. The ROM 10 also contains subprograms for selectively generating both a histographic log and a time domain log. The pacing program conditionally calls one of these subprograms for each occurrence of a sensed ventricular event (heartbeat) preceded by a ventricular event. A pair of status flags determines which, if either, of these subprograms is called. Random Access Memory 30 provides the temporary storage required by all programs, including the data logging subprograms. It also provides storage for the data accumulated in the logging process. The telemetry subprogram controls the additional status flags associated with data logging and to transmit the accumulated log data to the external programmer 42.

Figure 3:
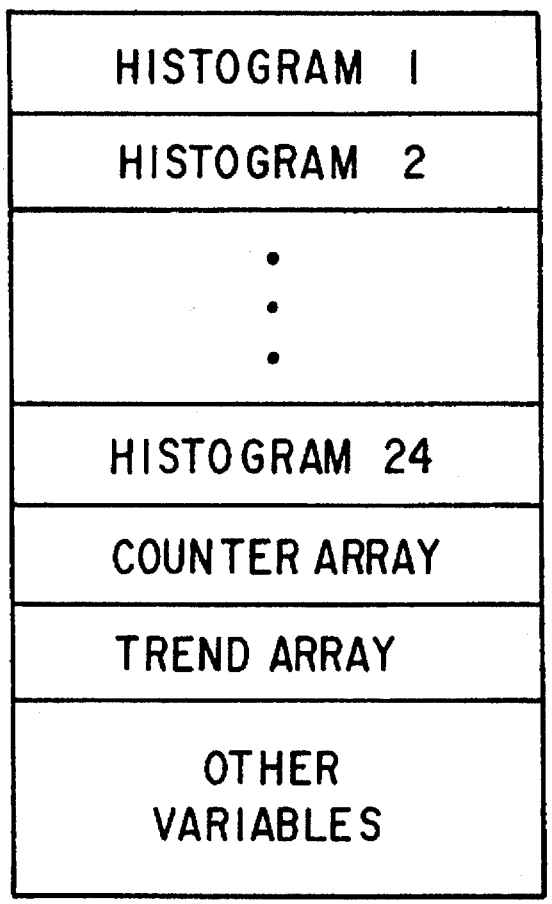
FIG. 3 is a memory map for the HRV log in accordance with the present invention.

Although a histographic HRV log may be implemented with a range of parametric values, for this description a square array of bins, e.g., 16×16 bins with each bin being four bits deep, is assumed. FIG. 3 shows a memory map of the region of Random Access Memory 30 used to generate such a log. Each two-dimensional histogram is packed into a 128 byte block of memory designated Histogram 1 to Histogram 24. Each byte contains two 4-bit bins. The counter array contains a one-byte counter for each bin of the histogram array or for 16×16 bins, 256 bytes are needed. These comprise a set of working counters which operate cooperatively with a histogram bin storage array, which is also a counter array, to perform logarithmic compression of the histogram data as it is accumulated. For each bin, the corresponding counter in the counter array functions as a variable weight pre-scaler for the histogram bin counter, i.e., the prescale value increases in accordance with the log of the number of events for a given bin.

TABLE 1

| Bin Counter | Event Count | Pre-Scale Divisor |
| --- | --- | --- |
| 0 | 0 | 1 |
| 1 | 1 | 1 |
| 2 | 2 | 1 |
| 3 | 3 | 1 |
| 4 | 4–7 | 4 |
| 5 | 8–11 | 4 |
| 6 | 12–15 | 4 |
| 7 | 16–19 | 4 |
| 8 | 20–51 | 32 |
| 9 | 52–83 | 32 |
| 10 | 84–115 | 32 |
| 11 | 116–147 | 32 |
| 12 | 148–403 | 256 |
| 13 | 404–659 | 256 |
| 14 | 660–915 | 256 |
| 15 | 916–1171 | 256 |

Table 1 shows how the pre-scale divisor varies to yield a logarithmically compressed count in the corresponding histogram bin counter. For the first four hits, each hit increments the bin counter by one. As used herein, the term "hit" is used to indicate when a measured RR interval and a computed absolute value of the difference in successive RR intervals fall within the range of a given bin. Upon a bin count reaching four, the pre-scale divisor is changed to four. Thus, the bin counter is not again incremented until the eighth hit. The pre-scal divisor also switches to 32 and then to 256 when the bin count reaches 8 and 12 respectively. As the pre-scale divisor is progressively incremented, the higher values of the bin counter acquire a greater weight, i.e., higher bin counter values represent a greater range of hits.

Figure 4:
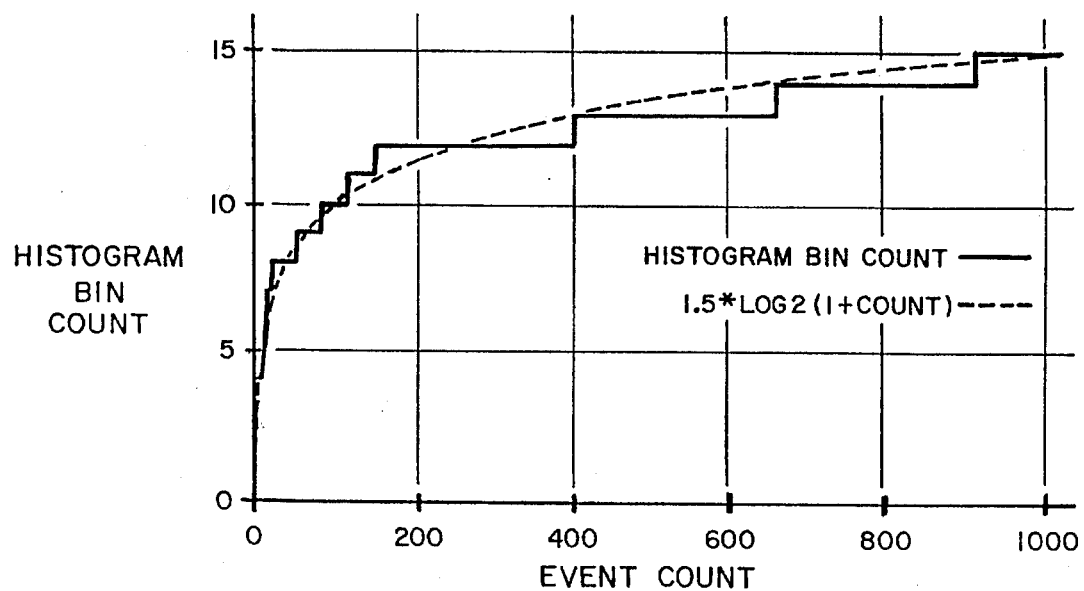
FIG. 4 is a plot of histogram bin counters vs. beat-to-beat difference in R-R interval.

The solid stepped line of FIG. 4 graphically shows the value of the histogram bin counter as a function of input event counts, where an input event is a beat-to-beat difference which is within the range of a given histogram bin. The results shown graphically in FIG. 4 are produced by an algorithm based on Table 1. Note that these results generally correspond to the theoretical logarithm of the input event count which is shown as a dashed line in FIG. 4.

Figure 5:
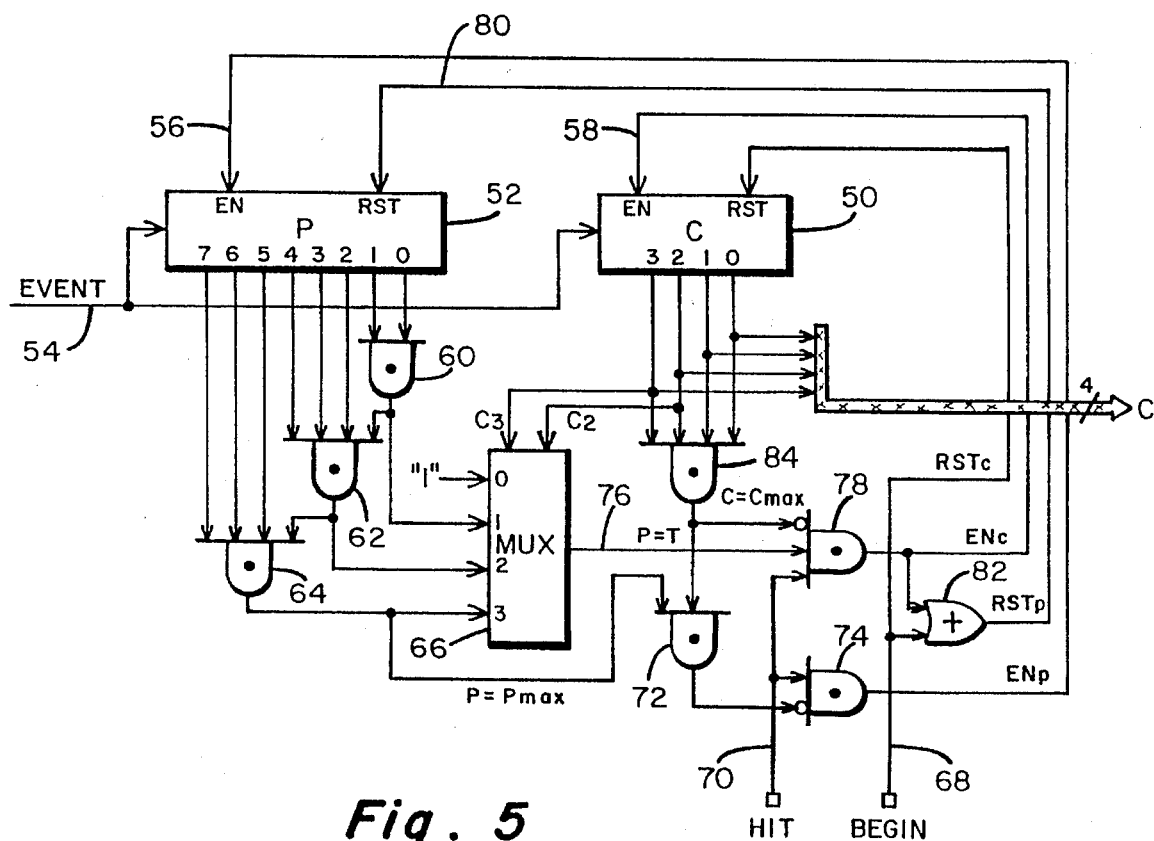
FIG. 5 is a logic block diagram of the logarithmic compression algorithm employed in implementing the present invention.

The logarithmic compression algorithm is implemented in hardware as illustrated in the logic block diagram of FIG. 5. As will be explained, it is also implementable in software. With reference to FIG. 5, counter 50 is shown as a 4-bit synchronous counter whose count value corresponds to an instant bin of the histogram array. Counter 52 is an 8-bit synchronous counter corresponding to the counter from the aforementioned counter array which is paired with counter 50 to function as a pre-scaler. Each heartbeat generates a signal on event line 54 which is connected to the clock inputs of counters 50 and 52. Thus, the counters are incremented in response to a heartbeat event when their respective count enable lines, 56 and 58, are active. AND gates 60, 62 and 64 decode the outputs of counter 52 for values of 3, 31 and 255 respectively. Multiplexor 66 selects one of these decode outputs depending upon the permutations of the two most significant bits of counter 50. Thus, the states of counter 50 equal to 00xx, 01xx, 10xx and 11xx invoke pre-scale divisors of 1, 4, 32 and 256 respectively. Counters 50 and 52 are cleared by a signal on "Begin" line 68. A logical "1" on hit line 70 signals that the beat-to-beat difference is within a given bin and is to be counted by counter pair 50 and 52. The output of AND gate 72 remains ZERO unless count saturation, i.e., 1171 counts is reached. Thus, AND gate 74 remains enabled to activate clock enable line 56, causing counter 52 to be clocked by the event signal 54. Initially, line 6 (P=T) is a logical "1" since the "0" input of multiplexor 66 is selected. Thus, each hit also fully enables AND gate 78 to activate counter enable line 58 and cause counter 50 to be incremented. At this time, reset line 80 is also activated, via OR gate 82, thus holding counter 52 cleared. When the count in counter 50 reaches 4 the "1" input of multiplexor 66 is selected. Now, AND gate 78 is enabled only when AND gate 60 is enabled to invoke a pre-scale value of 4. That is, every fourth hit increments counter 50 and resets counter 52. Pre-scale values of 32 and 256 are invoked as counting proceeds in counter 50 with the selection of multiplexor input "2" and then input "3". When both counters have filled, AND gates 64 and 84 are enabled to disable AND gates 74 and 78 which freezes the counters to prevent wrap around.

Figure 6:
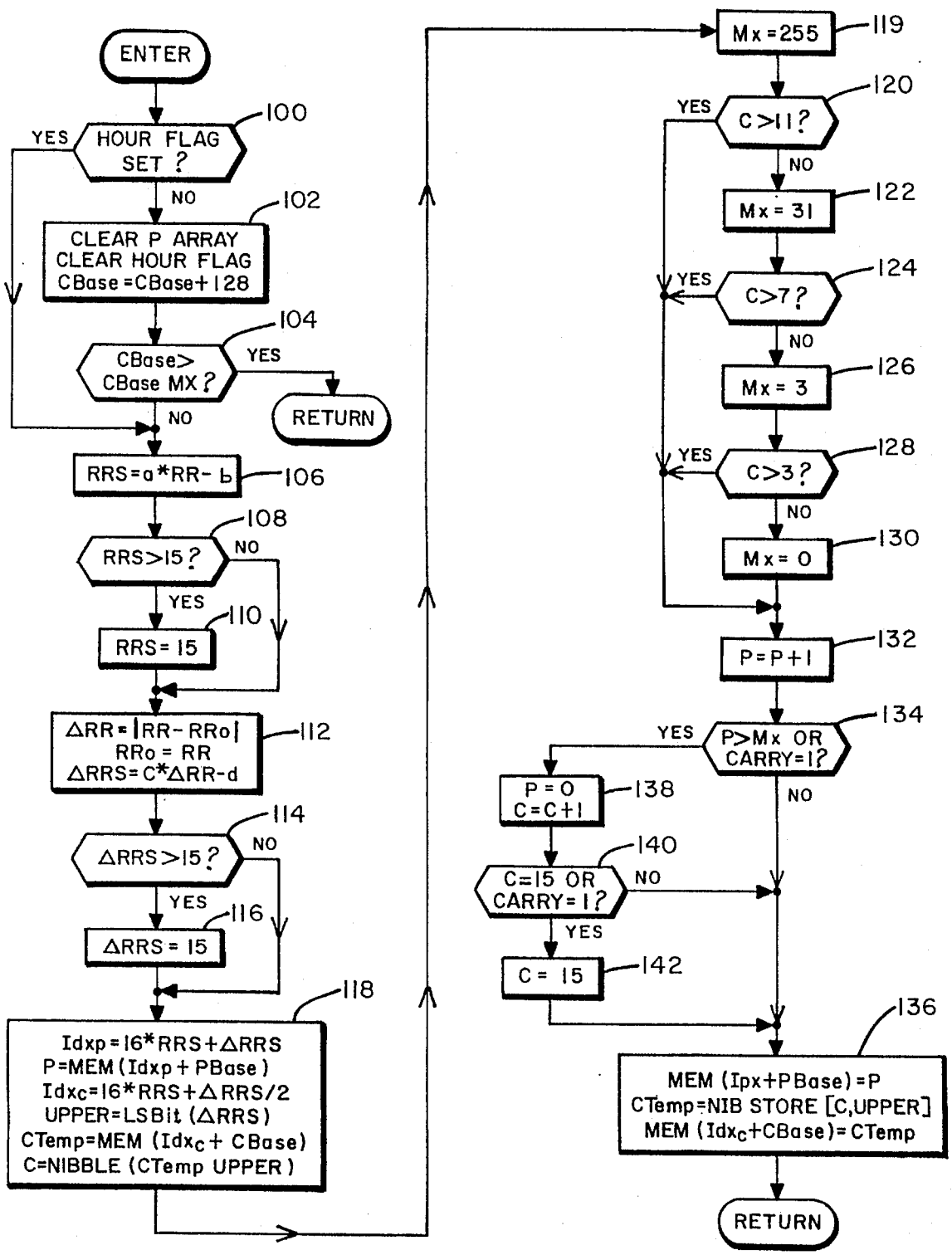
FIG. 6 is a software flow diagram showing the manner in which the algorithm of FIG. 5 can be implemented in firmware.

FIG. 6 is a software flow diagram which embodies the algorithm of FIG. 5 in firmware rather than hardware. Here, the counters C and P (50 and 52) of FIG. 5 are arrays of counters contained in RAM memory 30. This program is called by the main pacing program for each spontaneous heartbeat (sensed R wave) when the histographic log function is enabled. Each iteration of the program corresponds to a "Hit" signal in FIG. 5. The program fetches the specified counter pair from memory, operates on the counters in the manner of FIG. 5 and stores the results in memory. When initialized, the variable "Cbase" contains the base address corresponding to the beginning of the first histogram array of RAM memory 30. Similarly, "Pbase" contains the base address corresponding to RAM memory for the pre-scaler array. Variable "RR" contains a value indicative of the R-to-R interval, i.e., the elapsed time since the previous heartbeat. Upon being called, step 100 tests the Hour Flag. If an hour has elapsed, Cbase is adjusted at step 102 to point to the next histogram array. At step 104, Cbase is tested against a maximum Cbase limit, Cbase Mx, to assure that the program does not log data outside of the histogram arrays. If the Hour Flag is cleared, execution proceeds directly to step 106 where a scaled value of the R-to-R interval, "RRS", which corresponds to the bins of the histogram, is computed. For example, if the pacing program counts elapsed time at 128 counts/second, the variable RR in counts may range from 38 to 255 corresponding to a heart rate of 30 to 200 BPM. In this case, scaling coefficients a =0.069 and b=2.626 would be appropriate. Steps 108 and 110 test the value of RRS and clip it, if necessary, to assure that RRS is in the range of 0–15.

In a similar manner, steps 112–116 compute a scaled value of the beat-to-beat difference $\Delta$RRS which ranges from 0–15. At step 112, the absolute difference of the instant R-to-R interval (RR) and the previous R-to-R interval ($RR_0$) is computed. Next $RR_0$ is set equal to RR to be available for the next iteration. Scaling coefficients c=0.25 and d=0 would be appropriate to scale $\Delta$RRS to a range of 0–15. Variables RRS and $\Delta$RRS now define the bin in the two-dimensional histogram which is to be incremented. At step 18, RRS and $\Delta$RRS are multiplied to compute an index which identifies the relative position of the subject bin in RAM memory 0.

Variable, P, is fetched from the counter array of RAM memory 30 using an address which is the sum of "$Idx_p$" and "Pbase". $Idx_p$, itself, is an address index for a linear bank of memory with no offset and is used to point to P values. Since the C counters are 4-bit counters which are packed two per byte, $Idx_c$ is formed as in step 118 of FIG. 6. The least significant bit of $\Delta$RRS is saved to make a selection of either the upper or lower nibble to thus unpack the data. Variable C is fetched from the histogram array of memory 30 using an address which is the sum of $Idx_c$ and Cbase. Steps 120–130 test the state of counter C to determine the value of Mx which corresponds to the value of the pre-scale divisor per Table 1. Counter P is incremented at step 132 and tested against Mx at step 134. If P is less than or equal to Mx and if the carry flag is equal to 0, execution passes directly to step 136 which stores the current values of P and C using the indexes previously described. C must be packed back into memory without disturbing its associated nibble. Following step 136, execution is passed back to the main pacing program. Alternatively, if at step 134 counter P is greater than Mx or the carry flag is "1" then, at step 138, P is cleared and counter, C, is incremented. Steps 140 and 142 clip C at a maximum of 15 to prevent wrap around. For simplicity, the event counter P of FIG. 6 has been described as being an 8-bit counter. Logarithmic compression may also be accomplished with different length counters by computing $N_x = 2^c - 1$. Alternatively, other forms of monotonic, non-linear mapping may implemented with a ROM look-up table.

The time domain log is comprised of sequential pairs of data where each data pair describes heart rate variability for a 5-minute interval. The data pair is comprised of the mean value of the R-to-R interval and the variance of the R-to-R interval. The external pacemaker programmer, that is not subject to power constraints, extracts the square root from the variance to obtain the standard deviation external to the implanted device.

There is more than one approach to calculating variance. The direct approach is inferior to the indirect method. The direct method for estimating the variance of RR is:

$$\sigma_{RR}^2 = <\overline{RR^2}> - <\overline{RR}>^2$$

The use of this approach requires separate and simultaneous calculation of the 1st and 2nd moments of the data. The approach is numerically ill conditioned, especially when the mean RR is on the order of the standard deviation. Further, fixed-point INTEGER math is poorly suited to this approach, since it introduces large errors in both moment estimates, which when subtracted, yield a poor estimate of variance.

The indirect method provides an improvement in numerical performance:

$$\sigma_{RR}^2 = <[RR - \overline{RR}]^2>; \overline{RR} = <RR>$$

If the mean is available prior to estimating variance, then this method works fine. For a process with a non-zero mean, subtracting out the mean prior to accumulation reduces the size of the numbers involved and avoids the final subtraction. However, it is not possible to know the mean in advance nor is it desirable to store the set of RR values in an array such that the mean could be calculated followed by the variance. Although the indirect method is preferred, modifications are still required to make the RR variance calculation tractable in an implantable pacemaker.

The instance invention employs a novel variation of the indirect method, where an estimate of the mean is substituted. The resulting variance can be corrected after all the data values in the current 5-minute period have been seen. A modified expression for the mean RR is required to instrument this.

The usual summation required to evaluate the mean is not necessary with RR interval data when the period of integration is fixed to a constant interval of time. This is the case when calculating the mean RR interval as:

$$\overline{RR}(n) = \sum_{i \in \text{Period}(n)} RR(i)/N(n)$$

where N(n) is the number of RR intervals in the current period. While N(n) is unknown until the end of the current period, the sum of all the intervals, end-to-end over 5-minutes, is a constant 300 seconds. This feature is a little unusual, but it greatly simplifies what must be done.

$$\overline{RR}(n) = \text{SUM}/N(n) \; ; \; \text{SUM} = \text{a constant}$$

As indicated above, the variance of RR can be written as the sum of a variance estimate and an error term.

$$\sigma_{RR}^2(n) = \sigma_{est}^2(n) + \text{Error}(n)$$

The estimated variance is simply expressed:

$$\sigma_{est}^2(n) = \left(\frac{1}{N_1}\right) \sum_{i=1}^{N_1} [RR(i) - \overline{RR}(n-1)]^2$$

$$\sigma_{est}^2(n) = <RR^2> + \text{SUM}^2 \left[ \left(\frac{1}{N_0}\right)^2 - \frac{2}{N_0 N_1} \right]$$

Where $N_0 = N(n-1)$ $N_1 = N(n)$

But the exact expression for the variance of RR is $$\sigma_{RR}^2 = <RR^2> - (\text{SUM}/N_1)^2$$

Combining the information in the immediately preceding two equations yields:

$$<RR^2> - (\text{SUM}/N_1)^2 =$$

$$<RR^2> + \text{SUM}^2 \left[ \left(\frac{1}{N_0}\right)^2 - \frac{2}{N_0 N_1} \right] + \text{ERROR}(n)$$

Simplifying and solving for the error correction gives:

$$\text{Error}(n) = -(\text{SUM})^2 \left[ \left(\frac{1}{N_0^2}\right) + \left(\frac{1}{N_1}\right)^2 - \frac{2}{N_0 N_1} \right]$$

An expansion of the error function above provides a correction which may be practically computed in a pacemaker's microprocessor. After some manipulation and retaining, only the first two terms in the expansion, the above error correction equation reduces to:

$$\text{Erro.}(n) \approx -\left(\frac{\text{SUM}^2}{N_0^4}\right) \left[ \Delta N^2 - 2\frac{\Delta N^3}{N_0} \right]$$

The corrected expression for the variance becomes:

$$\sigma_{RR}^2(n) = \left[ \frac{1}{N_1} \sum_{i=1}^{N_1} [RR(i) - \overline{RR}(n-1)]^2 \right] -$$

$$\left( \frac{\text{SUM}^2}{N_0^4} \lfloor \Delta N^2 - 2\frac{\Delta N^3}{N_0} \rfloor \right)$$

Where: $N_1 = N(n)$
$N_0 = N(n-1)$
$\Delta N = N(n) - N(n-1)$
$RR(n-1) = \text{SUM}/N(n-1)$ The next step is to apply node scaling to the accumulation step in the preceding equation. During the simulation of RR intervals, values which occasionally exceeded 255 were observed. This was with an RR resolution of ¹⁄₁₂₈ or 128 counts corresponding to 1 second. In order to avoid clipping, all RR values were right shifted one bit. This allows the inputs to the accumulator to be represented in 8-bits.

Further scaling is required to insure that the accumulation sum fits within a 16-bit representation. To accomplish the above, the variance equation is modified:

$$\sigma_{RR}^2(n) = \left[ \frac{\sum_{i=1}^{N_1} [2(1/2RRi - 1/2\overline{X}_0)]^2/\alpha}{(N_1/\alpha)} \right] - \left( \frac{SUM^2}{N_0^4} \right) \left[ \Delta N^2 - 2 \frac{\Delta N^3}{N_0} \right]$$

Figure 7:
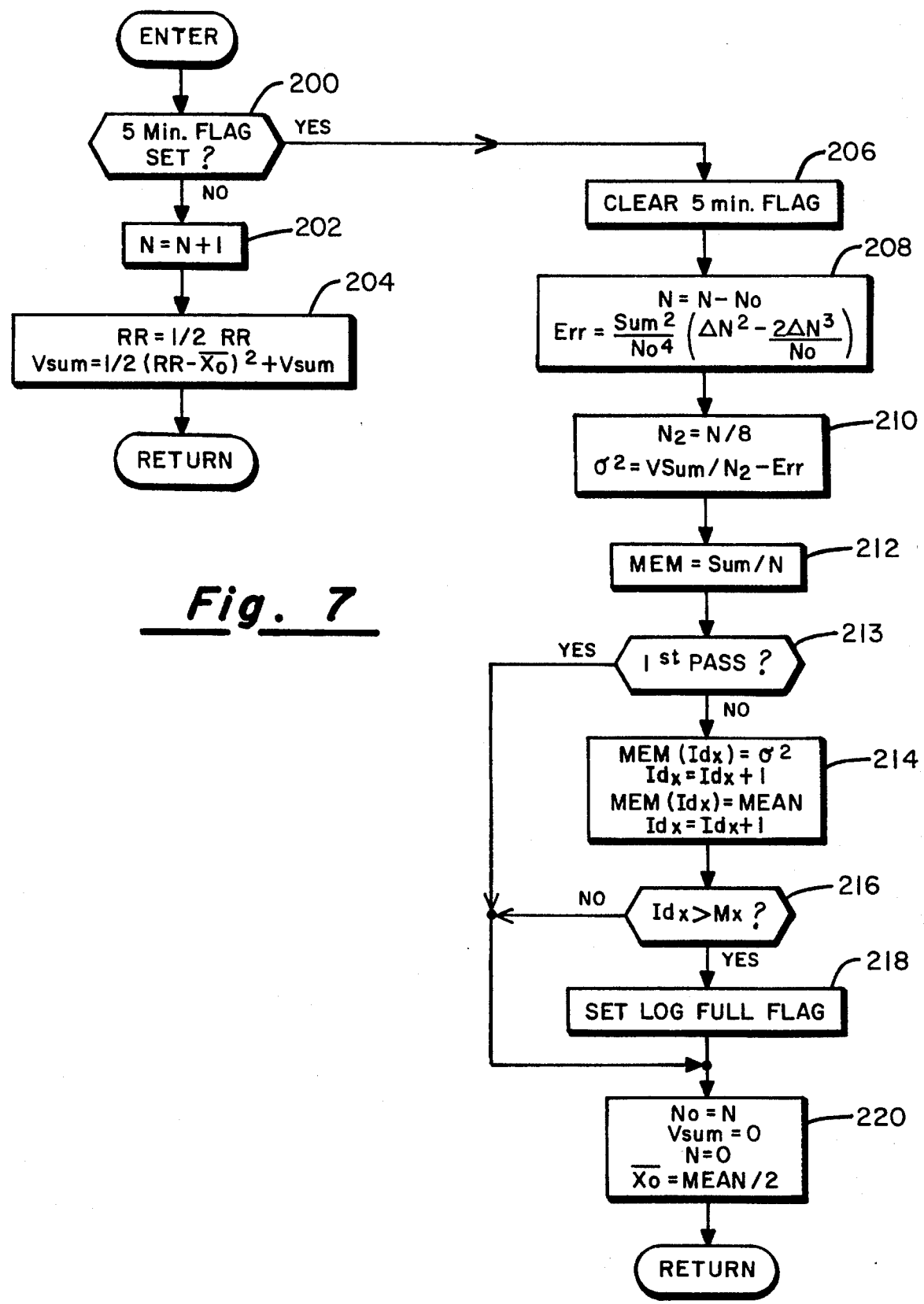
FIG. 7 is a program flow chart of the software routine used in generating a time domain log.

Where: $X_0 = RR(n-1)$
SUM=300*Countsec
Countsec=Counts/Second=128.
$\alpha = 8$ FIG. 7 shows a flow diagram of a subprogram which employs the novel variance algorithm to generate a time domain log. As with the histogram subprogram, this program is called by the main pacing program for each spontaneous heartbeat (sensed R wave) when the time domain log function is enabled and passes the variable RR indicative of the R-to-R interval. Upon initialization, the variable, N, which counts the number of events in a 5-minute period, is cleared, the variable, Idx, is set to a value corresponding to the first address of the log data array and a dummy, non-zero value is chosen for No. When the subprogram is called, step 200 tests the 5-Minute Flag, which indicates the end of the 5-minute sampling period. If this flag is cleared, step 202 increments the variable N. At step 204, RR is shifted right one place to prevent overflow in subsequent calculations. Variable, $\overline{X}_0$ is one half of the mean value computed for the preceding period. This provides the estimate for the mean of the current period. The difference between the adjusted value of RR and $\overline{X}_0$ is squared, multiplied by ½ and added to VSum. Sixteen-bit multiplication is used to perform the square operation and VSum is accumulated in a register.

As the subprogram is re-entered with each new value of RR, VSum progressively accumulates the sum of the squares of the difference between RR and the estimated mean. If the 5-minute flag is set, the subprogram branches to compute the mean value and the square of the variance. At step 208, which is repeated every five minutes, the instant and previous values of N are used to compute the correction required to compensate for the difference between the estimated and actual value of the mean value. At Step 210 The variable $\sigma^2$ is computed. First, N is divided by 8 ($\alpha = 8$), then VSum is divided by the scaled value of N. Finally, the error correction is subtracted to obtain the actual value. Overflow and truncation errors are minimized by employing well-known scaling techniques at steps 208 and 210. At step 212, the mean value of the R-to-R interval is computed by dividing a constant Sum by N. This computation relies upon the fact that for sinus rhythm the sum of the R-to-R intervals is a constant. Paced events are ignored and their time is thus subtracted from the 300 seconds. On the first pass after initialization, Step 214 is skipped. Otherwise, it stores the computed data in RAM memory 30, using Idx as a pointer. If Step 216 determines that Idx is greater than Mx, a Log Full Flag is set to inhibit the pacer program from making further calls to this subprogram, which would overrun the log data array. At step 220, $N_0$ is set equal to N to prepare for the next error calculation and N is cleared. The variable $\overline{X}_0$ is set to one half the Mean to provide a new estimate for the next set of calculations. With valid values of $N_0$ and $\overline{X}_0$ now established, subsequent calculations will be accurate and will be logged at step 214.

What is claimed is:

1. A cardiac assessment device including a microcontroller having memory means for storing a program and data at addressable locations therein, the microcontroller being responsive to ventricular depolarization events for measuring RR intervals between successive ones of naturally occurring ventricular depolarization events, comprising:

(a) means for computing an absolute value of a difference in the RR interval for successive naturally occurring ventricular depolarization events;

(b) means for computing a histographic log comprising a statistical distribution of a plurality of RR intervals and an the absolute value of the difference in the RR intervals occurring in a predetermined time period;

(c) means for storing said histographic log in the memory means, and (d) means for developing from the RR intervals a time domain log of heart rate variability.

2. The cardiac assessment device as in claim 1 and further including an external programmer and means for telemetering the stored histographic log and time domain log to the external programmer.

3. The cardiac assessment device as in claim 2 wherein the memory means comprises:

(a) a plurality of memory locations for storing a histographic log as a two-dimensional histogram array, wherein the first dimension is proportional to the RR interval and the second dimension is proportional to the absolute difference between successive RR intervals.

4. The cardiac assessment device as in claim 3 wherein each of the memory locations corresponds to a bin, where each bin comprises one element of the two-dimensional histogram array.

5. The cardiac assessment device as in claim 4 wherein the computing means includes means for generating an address that identifies, on a beat-to-beat basis, particular bin of the two-dimensional histogram array that should be incremented.

6. The cardiac assessment device as in claim 4 wherein the computing means further includes data compression means for conditionally incrementing a given bin as a function of current value contained in such given bin and a number of events where said absolute difference in successive RR intervals is within predetermined range assigned to that given bin since that given bin had last been incremented.

7. The cardiac assessment device as in claim 6 wherein the data compression means includes variable weight pre-scaling means whose scale value is logarithmically related to a beat-to-beat difference in successive RR intervals to produce a logarithmically compressed result in the two-dimensional histogram array.

8. The cardiac assessment device as in claim 4 wherein the means further includes a counter array, each counter in the array corresponding to one bin of the two-dimensional histogram array for pre-scaling counts to effect data compression.

9. The cardiac assessment device as in claim 4 wherein the external programmer includes a microprocessor and a graphics display coupled to the microprocessor for presenting said two-dimensional histogram arrays and wherein the element stored in each bin is indicated by a particular color or shade on said graphics display.

10. A cardiac assessment device including a microcontroller having memory means for storing a program and data at addressable locations therein, said microcontroller being responsive to ventricular depolarization events for measuring a RR interval between successive ones of naturally occurring ventricular depolarization events, comprising:

(a) means for generating a time domain log based upon the RR intervals occurring during a predetermined period of time, said generating means including computing means for calculating data comprising a mean value of the RR intervals and a square of a standard deviation of the RR intervals occurring during said predetermined period of time;

(b) an external device: and (c) means for telemetering the mean value of the RR interval and the standard deviation data to the external device.

11. The cardiac assessment device as in claim 10 wherein said means comprises a plurality of paired memory locations, a first location of each pair storing a value proportional to the mean of the RR intervals occurring in the predetermined period of time, a second location of each pair of locations storing a value proportional to the square of the standard deviation of the RR intervals occurring during the predetermined period of time.

12. The cardiac assessment device as in claim 11 wherein the square of the standard deviation is computed using an estimate of the mean value of the RR interval.

13. A cardiac assessment device comprising a microcontroller having memory means for storing a program and data at addressable locations therein, said microcontroller being responsive to ventricular depolarization events for measuring a RR interval between successive ones of naturally occurring ventricular depolarization events; and means for developing from the RR interval a histographic log of heart rate variability and a time domain log of heart rate variability.

14. The cardiac assessment device as in claim 13 and further including: an external device: and means connected to the cardiac assessment device for telemetering the histographic log and the time domain log of heart rate variability to the external device.

15. In a cardiac assessment device responsive to ventricular depolarization events, a method for logging heart rate variability (HRV) data over a predetermined period, comprising the steps of:

(a) measuring a RR interval between successive ones of naturally occurring ventricular depolarization events;

(b) calculating an absolute value of a difference between successive ones of the measured RR intervals;

(c) calculating data relating to a statistical distribution of a plurality of RR intervals measured in step (a) and the absolute value of the difference in the RR intervals calculated in step (b);

(d) logarithmically compressing the data calculated in step (c); and (e) storing the results of step (d).

16. The method as in claim 15 and further including the step of telemetering the stored results to an external device.

17. In a cardiac assessment device of the type including a microcontroller having memory means for storing a program and data at addressable locations therein, said microcontroller being responsive to ventricular depolarization events for measuring a RR interval between successive ones of naturally occurring ventricular depolarization events, a method for logging heart rate variability (HRV) data over a predetermined period comprising the steps of:

(a) calculating by means of the microcontroller a mean value of RR intervals occurring during a predetermined period of time;

(b) determining an estimate of the mean value of the RR interval to compute in said microcontroller a square of a standard deviation of the RR intervals occurring during said predetermined period of time;

(c) generating a time domain log of the mean values calculated in step (a) and of the square of the standard deviation of RR intervals determined in step (b); and (d) telemetering the time domain log to an external device.

18. A cardiac assessment device including a microcontroller having memory means for storing a program and data at addressable locations therein, the microcontroller being responsive to ventricular depolarization events for measuring RR interval between successive ones of naturally occurring ventricular depolarization events, comprising:

(a) means for computing an absolute value of a difference in the RR interval for successive naturally occurring ventricular depolarization events;

(b) means for computing a result indicative of a statistical distribution of a plurality of RR intervals and a result indicative of the absolute value of the difference in the RR intervals occurring in a predetermined time period;

(c) means for storing said results in the memory means, the memory means storing a two-dimensional histogram array at the addressable locations, the first dimension is proportional to the RR interval and the second dimension is proportional to the absolute difference between successive RR intervals, each addressable location corresponding to a bin and each bin being one element of the two-dimensional histogram array;

(d) means for telemetering the stored results to an external programmer; and (e) the means for computing including means for generating addresses that identifies on a beat-to-beat basis a particular bin of the two-dimensional histogram array that should be incremented.

19. The cardiac assessment device as in claim 18 wherein the computing means further includes data compression means for conditionally incrementing a given bin as a function of a current value contained in such given bin and a number of events where said absolute difference in successive RR intervals is within a predetermined range assigned to that given bin since that given bin had last been incremented.

20. The cardiac assessment device as in claim 19 wherein the data compression means includes variable weight pre-scaling means whose scale value is logarithmically related to a beat-to-beat difference in successive RR intervals to produce a logarithmically compressed result in the two-dimensional histogram array.

21. The cardiac assessment device as in claim 18 wherein the storing means further includes a counter array, each counter in the counter array corresponding to one bin of the two-dimensional histogram array for pre-scaling counts to effect data compression.

22. The cardiac assessment device as in claim 18 wherein the external programmer includes a microprocessor and a graphics display coupled to the microprocessor for visually presenting said two-dimensional histogram arrays and wherein the element stored in each bin is indicated by a particular color or shade of gray on said graphics display.

23. A cardiac assessment device including a microcontroller having memory means for storing a program and data at addressable locations therein, said microcontroller being responsive to ventricular depolarization events for measuring a RR interval between successive ones of naturally occurring ventricular depolarization events, comprising:

(a) means for generating a time domain log based upon the RR intervals occurring during a predetermined period of time, said generating means including computing means for calculating data comprising a mean value of the RR intervals and a square of a standard deviation of the RR intervals occurring during said predetermined period of time;

(b) said memory means comprising a plurality of paired memory locations, a first location of each pair storing a value proportional to the mean of the RR intervals occurring in the predetermined period of time, a second location of each pair of locations storing a value proportional to the square of the standard deviation of the RR intervals occurring during the predetermined period of time, the square of the standard deviation being computed using an estimate of the mean value of the RR interval;

(c) an external device; and (d) means for telemetering the mean value of the RR interval and the standard deviation data to the external device.

* * * * *

UNITED STATES PATENT AND TRADEMARK OFFICE
CERTIFICATE OF CORRECTION

PATENT NO. : 5,603,331
DATED : February 18, 1997
INVENTOR(S) : Jan P. Heemels, M. Carlson, Julio C. Spinelli It is certified that error appears in the above-indentified patent and that said Letters Patent is hereby corrected as shown below:

In claim 5, line 39, after "basis," insert -- a --;

In claim 6, line 47, after "within" insert -- a --;

In claim 8, line 56, at the beginning, before "means" insert -- storing --;

In claim 9, line 62, after "for" insert -- visually --;

In claim 11, line 17, after "said" insert -- memory --;

In claim 18, line 25, after "locations," insert -- wherein --

Signed and Sealed this

Sixth Day of May, 1997

*Attest:*

BRUCE LEHMAN

*Attesting Officer*  *Commissioner of Patents and Trademarks*